United States Patent [19]
Huddleston et al.

[11] Patent Number: 5,788,705
[45] Date of Patent: Aug. 4, 1998

[54] METHOD AND APPARATUS FOR INTRAOPERATIVE REAPPROXIMATION OF A HIP JOINT

[75] Inventors: H. Dennis Huddleston, Encino, Calif.;
Ian P. Murray, Phoenix, Md.;
Lawrence F. Shaffer, III, New Freedom, Pa.

[73] Assignee: Osteoimplant Technology Incorporated, Hunt Valley, Md.

[21] Appl. No.: 575,865

[22] Filed: Dec. 20, 1995

[51] Int. Cl.$^6$ ............................................. A61B 17/58
[52] U.S. Cl. ................................... 606/102; 606/72
[58] Field of Search .................... 606/72, 75, 101, 606/102, 151, 103, 104, 54, 60, 67, 62, 64, 74

[56] References Cited

U.S. PATENT DOCUMENTS

| | | | |
|---|---|---|---|
| 3,762,404 | 10/1973 | Sakita | 128/78 |
| 4,361,144 | 11/1982 | Slätis et al. | 606/54 |
| 4,730,609 | 3/1988 | McConnell | 606/72 |
| 4,978,350 | 12/1990 | Wagenknecht | 606/72 |
| 5,209,756 | 5/1993 | Seedhom et al. | 606/151 |
| 5,342,396 | 8/1994 | Cook | 606/219 |

FOREIGN PATENT DOCUMENTS

| | | | |
|---|---|---|---|
| 2659224 | 9/1991 | France | 606/102 |
| 8201308 | 4/1982 | WIPO | 606/219 |

OTHER PUBLICATIONS

"Internal Fixation of Femoral Neck," *Journal of Bone and Joint Surgery*, vol. 27, #3, Jul. 1945, p. 523.

Vitallium (TM) catalog, 1964, pp. 44, 70.

McGee et al., "A Simple Method of Obtaining Equal Leg Length," *Clinical Orthopedics and Related Research*, 1985, pp. 269–270.

Bal, "A Technique For Comparison of Leg Lengths During Total Hip Replacement", *The American Journal of Orthopedics*, pp. 61–62 (Jan. 15, 1996, date of mailing).

Harris, "A New Approach to Total Hip Replacement Without Osteotomy of The Greater Trochanter", *Clinical Orthopaedics and Related Research*, No. 106, pp. 19–26, (1975).

Knight, "Accurate Determination of Leg Lengths During Total Hip Replacement", *Clinical Orthopaedics and Related Research*, pp. 27–28, (1977).

*Primary Examiner*—Michael Buiz
*Assistant Examiner*—Julian W. Woo
*Attorney, Agent, or Firm*—Foley & Lardner

[57] ABSTRACT

A method and apparatus for realigning the pelvis, femoral head, femur, trochanter, and acetabulum of a patient during a hip joint replacement procedure being performed on the patient. Prior to replacing the hip of the patient with a prosthesis, a pin is inserted into the patient's pelvis. The pin has a plurality of weakened areas of reduced cross-section formed along its length so that the pin is capable of being bent at approximately a 90° angle at each of the weakened areas. The pin is used to establish a point of reference as to the leg length and the desired orientation of the prosthetic joint.

18 Claims, 3 Drawing Sheets

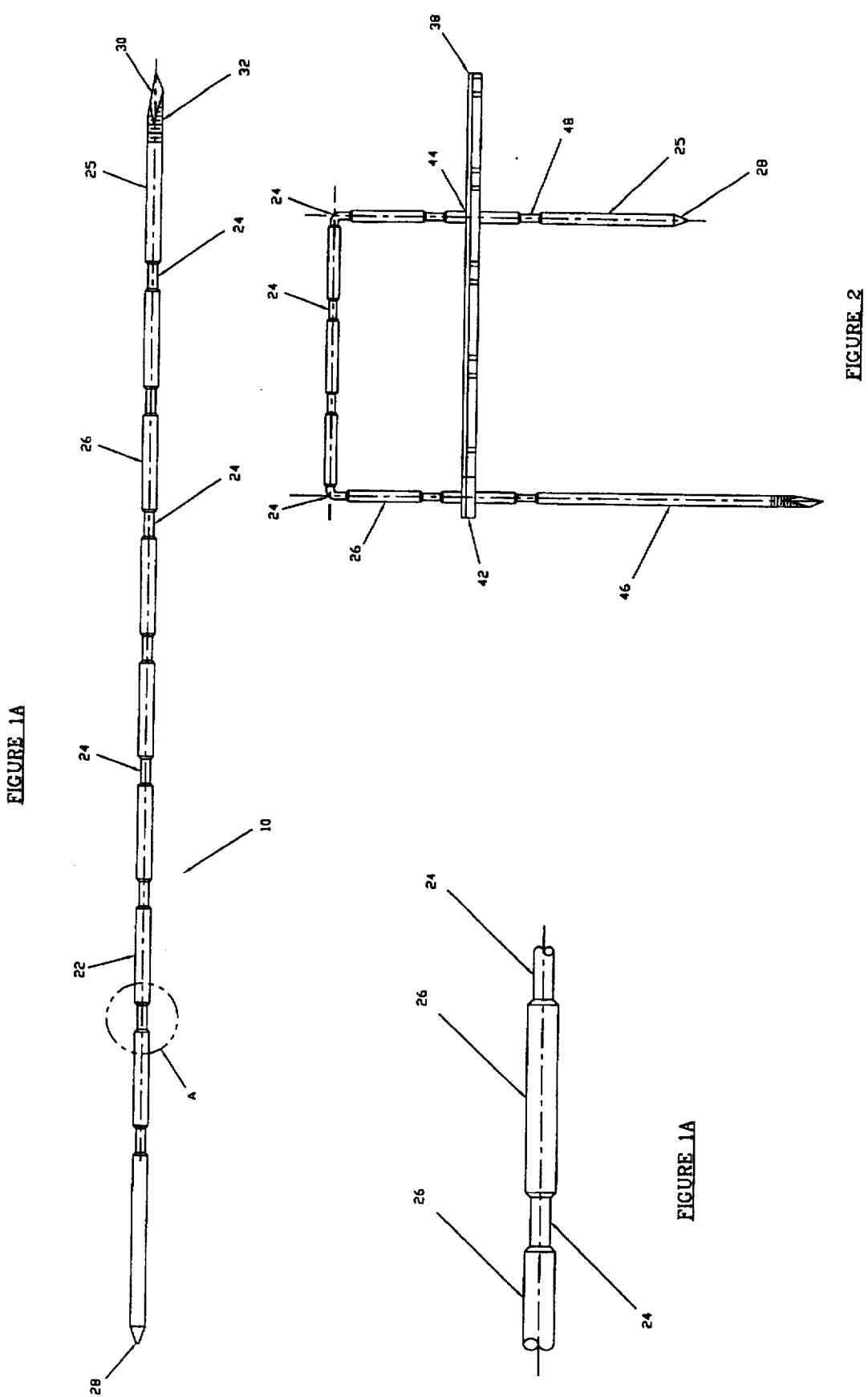

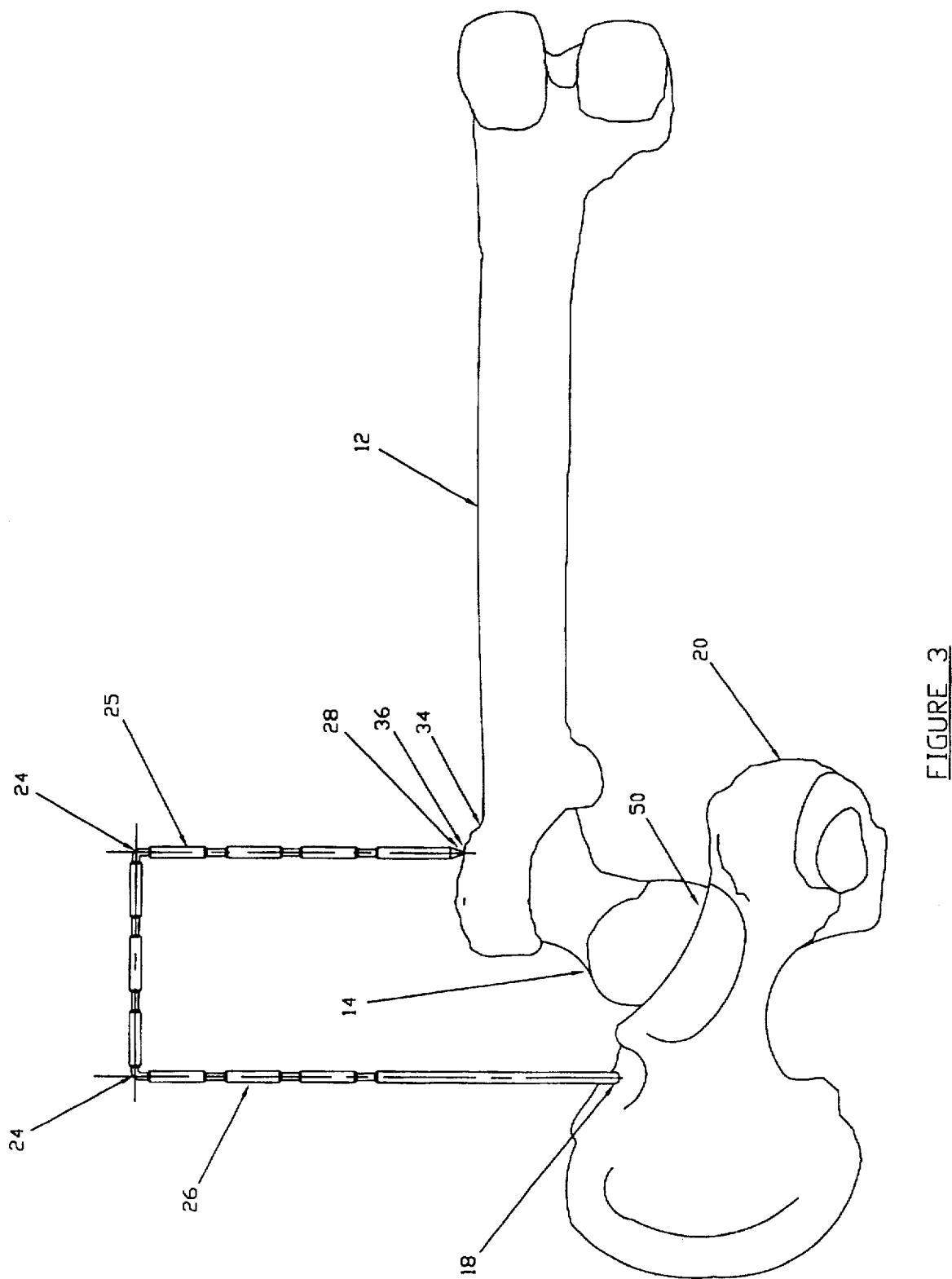

METHOD AND APPARATUS FOR INTRAOPERATIVE REAPPROXIMATION OF A HIP JOINT

BACKGROUND OF THE INVENTION

1. Field of the Invention

The present invention relates to surgical hip replacement techniques and in particular to methods and apparatus for optimizing the resultant hip joint configuration during insertion of a hip prosthesis.

2. Description of Related Art

Hip replacement procedures are widely employed to counter the effects of injury or disease, such as arthritis. In general, a total hip replacement procedure involves removing the femoral head at the uppermost part of the femur, reaming and broaching the interior of the femur after removal of the femoral head, and then insertion of a prosthesis into the hollowed out femur. In many of the hip replacement procedures, depending upon the extent of injury or disease, the acetabulum, the bowl shaped surface in the pelvis which receives the femoral head, is also reamed and fitted with a prosthetic cup or shell.

By way of background, the following observations and definitions are important.

Leg length inequality occurs frequently after total hip replacement. The operated leg is more commonly lengthened than shortened; reported lengthening averages between 7 and 16 mm with a range between 2 and 29 mm. Occasionally, the operated leg is deliberately lengthened to improve hip stability. Usually, the inequality is unintended, resulting from the real difficulty of determining leg length accurately during surgery.

Lengthening of the operated leg can cause patient dissatisfaction from discomfort, imbalance, low back pain, neuralgia, sciatic nerve injury, limp or the need for a shoe lift on the unoperated side. Increased abductor tension caused by lengthening can cause relative abduction contracture and thereby add an apparent lengthening to a true lengthening, further aggravating the problem.

Since lengthening occurs proximal to the femoral insertion of the hip capsule, lengthening the leg and leaving the anterior capsule intact can cause an internal rotation contracture of the hip. Conversely, leg lengthening coupled with an intact posterior capsule can result in an external rotation contracture of the hip.

Shortening the operated leg can result in abductor weakness, hip instability or the need for a shoe lift on the operated side.

Changes in offset may have unforseen consequences. Femoral offset is the shortest (i.e., perpendicular) distance between the center of the femoral head and the central longitudinal axis of the femur. Acetabular offset is the shortest distance between the acetabular center of rotation and the central axis of the body. Hip offset is the sum of the femoral and acetabular offsets. Medio-lateral changes in the locus of the lateral cortex of the greater trochanter are representative of changes in hip offset if the rotation of the hip remains constant. In the articulated hip, the center of rotation of the femoral head and of the acetabulum are a single locus.

Decreasing acetabular offset increases the effective abductor moment arm and may improve abductor function. Increasing femoral offset has the same result. It is likely that intrinsic abductor function is optimal when the direction of muscle pull and resting muscle length are restored to their original state through restoration of the greater trochanter to the isotrochanteric locus. For optimal abductor function without trochanteric advancement, there may be a delicate balance between the advantages of decreasing acetabular offset, increasing femoral offset, and restoration of the pre-operative hip offset and leg length.

Changes in hip mechanics engendered by changes in leg length and hip offset may contribute to implant wear and aseptic loosening.

In total hip replacement, leg length is determined by the level of the femoral neck resection, proximal and medial extent of acetabular reaming, final proximo-distal locus of the cup and the selected sizes of the modular elements of the implant. Hip offset is determined by the level of the femoral neck resection, femoral component neck angle, intrinsic offset of the femoral component, depth of acetabular reaming, final medio-lateral locus of the cup, and the selected sizes of the modular elements of the implant.

It is nearly impossible to correctly predict all these variables, and to accurately select from all these choices, by means of preoperative templating and planning alone.

More generally speaking, during the hip replacement surgical procedure, the original geometry of the hip joint is significantly modified. To ensure effective operation and use of the prosthetic joint, it is imperative that the femoral head and acetabulum prostheses be realigned in an appropriate configuration. That is, depending upon the condition of the patient's original pelvis and hip joint, the surgeon may want to either restore the component elements of the hip joint to their original position prior to surgery, or alternately, if the joint has been substantially misconfigured prior to the replacement procedure, reposition the joint, optimizing the realignment is commonly referred to as "normalizing" the geometry of the prosthesis. A hip joint which has been normalized has been optimized both as to leg length and as to offset or angular moment between the acetabulum and the femoral head. It has been determined that failure to correctly normalize the joint may result in increased wear of the plastic and metal parts of the prosthesis and thus, a reduced useful life thereof.

Accordingly, it is desirable to optimize the hip joint prosthesis prior to the completion of a hip replacement procedure.

Many surgeons rely on a subjective intraoperative estimate of soft tissue and ligament tension as a guide to leg length determination. Tissue tension can be misleading, being affected by the extent of soft tissue resection, the use of muscle relaxants as part of the anesthetic, alterations in offset, the amount of force used to distract the joint, and other factors.

Many surgeons erroneously believe that a line through the centers of the femoral heads corresponds to the level of the superior border of the greater trochanters, and use that level as a guide to length determination.

One proposed method of leg length measurement is by palpation of ankle malleoli and anterior superior iliac spines. The method is inaccurate in the unclothed, supine patient, and near impossible through several layers of drapes, with the patient in the lateral decubitus position.

A commonly used method of leg length and offset determination relies on preoperative templating of radiographs to estimate the center of hip rotation, the level of the femoral neck resection, and the size and placement of implant components to be used. However, hip offset varies with femoral rotation, and the magnification of radiographs varies with X-ray technique and patient size. Opaque markers placed in the field to determine magnification are not reliably accurate since marker placement is fairly critical and is usually left to an unsupervised technician, and accurate placement can be difficult even in experienced hands, especially in obese patients.

The degree of X-ray magnification varies greatly from patient to patient. Even if it were possible to easily, accurately and consistently determine the exact degree of radiographic magnification, manufacturers usually provide but a single set of hip implant outline acetate templates, the magnification of which is fixed somewhere between 105 percent and 120 percent. Accurate templating demands an exact determination of the magnification for each hip X-ray, and implant component templates which are matched to the magnification of those radiographs. This would require a complete set of templates for all possible magnifications.

The level of the femoral neck resection, as calculated by templating, is usually measured intraoperatively from the center of the femoral head. This can be difficult to estimate with a femoral head of normal shape, and impossible if the femoral head is deformed.

The superior junction of the lesser trochanter with the femur is a more reliable landmark, but measurement is still complicated by translation of preoperative radiograph units to real units of intra-operative measurement.

Another approach uses the top of the femoral head as the reference level. This method underscores the inexactness of the templating method in that at least one study showed a considerable number of patients still had length discrepancies ranging from 7 to 23 mm.

The extent of superior and medial acetabular reaming influences the final leg length. Medial acetabular reaming affects the hip offset. There is no accurate method to measure these acetabular variables during surgery, though the depth of the fovea (tear drop) serves as a landmark in the absence of other measuring aids.

The inaccuracies of templating, the difficulty of determining the correct level of femoral neck resection at surgery, the uncertainties created by acetabular reaming, and the variables occasioned by implant selection and placement make accurate intraoperative measurement imperative if the surgeon is to exercise control over the final leg length and hip offset.

An infrequently used method of leg length assessment is by intraoperative X-ray with the trial components in situ. The technique is expensive, time consuming, and difficult in an immobile, draped patient in the lateral decubitus position. The X-ray should include both hips, with the legs parallel, and the lesser or greater trochanters clearly visible. In many cases, X-rays are required more than once to fine-tune the final length, further adding to the expense.

Several reports have recommended a variety of methods and devices for intraoperative leg length measurement. However, all are rendered inaccurate by lack of a reliable method to reposition the leg before each measurement Harris (1975) describes a simple method of instrumented leg length measurement in which a threaded Steinman pin is drilled into the pelvis superior to the acetabulum. A ruler is used to make measurements from the pin to a mark on the greater trochanter. The flexion/extension leg position is outlined on the drapes with a pen. However, the marks are readily compromised by drape movement and no method is recommended to spatially fix the medio-lateral position of the leg.

Knight (1977) recommends a Steinman pin anchored in the iliac crest and bent to touch the greater trochanter. Pin anchorage is insecure and the pin tends to obstruct the operation.

Some surgeons utilize a combination of the Harris and Knight methods: a standard Steinman pin anchored in the pelvis just superior to the acetabulum is bent to touch the greater trochanter. However, a standard Steinmann pin is often too short in this application, requiring insertion through the main wound where it may obstruct the procedure or may be bent by the wound margins with changes in the position of the hip. Its length also renders it useless in many obese patients. A fully threaded pin often binds up soft tissues as it is being inserted or removed, and can theoretically cause injury to the inferior gluteal nerve and vessels in doing so. A fully threaded pin frequently breaks at the site of a right angled bend unless a very thick pin is used. However, a thick pin may require two sets of vice grips and much force to bend, often dislodging its anchorage in osteoporotic bone. A smooth pin has a tendency to dislodge from bone; or migrate medially into the pelvis, compromising hip offset measurements and possibly causing injury to intrapelvic structures.

A second Harris method uses a cumbersome, three pronged adjustable caliper. It measures length but not offset. The technique calls for "placing the extremity in a reproducible position but falls short in recommending a method to so.

Another system recommends two parallel pins to overcome the variability in the position of the operated leg. One pin is inserted into the pelvis and one into the greater trochanter. It is assumed that when the pins are parallel, the original hip position has been restored. However, the pins do not compensate for changes in hip flexion and extension, and the trochanteric pin is easily dislodged because of insecure anchorage. Small changes in the angle of either pin through migration can lead to large errors in leg length estimation. The method does not measure offset.

SUMMARY OF THE INVENTION

It is therefore an object of the present invention to provide a method for reconfiguring the mechanics and dimensions of the pelvis, femoral head, femur, trochanter, and acetabulum of a patient during a hip joint replacement procedure.

It is also an object to provide apparatus which is adapted to be readily used in conjunction with the above method.

It is a further object to provide a method which may be employed in determining both the appropriate leg length and offset of the joint.

It is still a further object to provide a method which allows a reference point to be established prior to replacing the patient's hip which is capable of being reproduced after the hip is replaced with a prosthesis.

It is yet an additional object to provide a kit which includes apparatus useful in a hip replacement procedure for determining the appropriate post-operative leg length and hip offset of the prosthesis.

In accomplishing these objects, the patient's leg adjacent the hip to be replaced is positioned into a fixed, molded cradle to ensure that any reference points established prior to replacing the hip are reproducible at a later point in the surgery. A specially adapted pin which has a plurality of weakened areas of reduced diameter formed about its length is then inserted into the pelvic bone. After insertion, the pin is preferably bent 90° at two of the weakened areas toward the joint which is to be replaced. The point where the pin intersects with the greater trochanter forms a reference point. The reference point is then marked directly on the patient, and a locking member is fastened onto the pin to ensure that the angular orientation of the pin is maintained. The pin, which remains inserted in the patient's pelvis, is then swung away from the operative site, and the hip replacement surgery proceeds. After replacement of the patient's hip, the bent pin is rotated back toward the operative site and the patient's leg is repositioned within the fixed, molded cradle. Using the marked location on the patient as a guide, the surgeon is able to properly align the hip joint and set the patient's leg length.

These and other features are described in the Figures and detailed description which follows.

BRIEF DESCRIPTION OF THE DRAWINGS

FIG. 1 is a side view of a surgical pin according to the present invention. FIG. 1A is blow-up of Detail A as shown in FIG. 1.

FIG. 2 is a side view of the surgical pin which is bent in substantially a U-shape and is held in position by a locking member according to the present invention.

FIG. 3 is a perspective view of a surgical site prior to hip replacement showing a surgical pin according to the present invention which has been inserted into the pelvis of a patient and has been bent into substantially a U-shape.

DETAILED DESCRIPTION OF THE PREFERRED EMBODIMENTS

Figure 4:
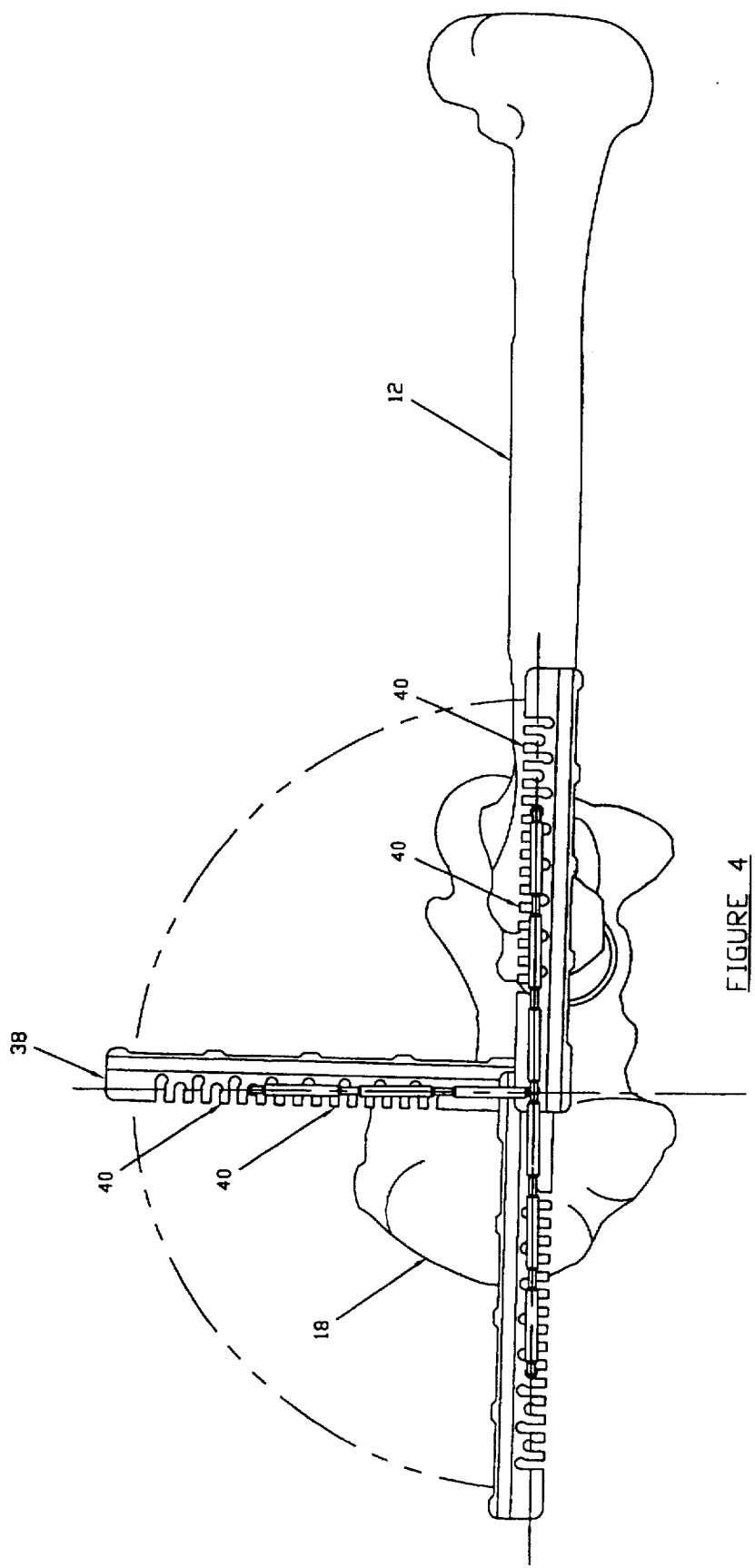
FIG. 4 is a plan view showing the rotation of the pin during surgery.

The present invention includes a method for realigning the pelvis, femoral head, femur, trochanter, and acetabulum of a patient during a hip joint replacement procedure which includes specifically designed apparatus for accomplishing the contemplated method. The patient may be a human or any animal which is capable of receiving a prosthetic hip, for example a dog, cat, monkey, and the like. However, at the present, the large percentage of hip replacements are performed on humans. According to the present invention, both pre- and post-hip replacement reference points are established. By comparing the post-hip replacement reference point with the pre-hip replacement reference point, it is possible to determine whether the leg length and/or angular offset of the prosthetic joint are properly configured.

Specifically, the intended leg length is estimated by comparison with the opposite hip on a preoperative AP X-ray of the pelvis, as well as clinical measurements using graduated wooden boards. If necessary, a scanogram is obtained. In most cases the object is the preservation of the preoperative leg length. The pre and post operative hip offset can be measured and compared on an AP X-ray of the pelvis with the hips internally rotated 20 degrees.

The patient's leg is positioned into a fixed location, for example, a molded cradle so that the femur 12 assumes a specific alignment with respect to the hip joint 14. In a preferred embodiment, a molded cradle in the form of a vacuum surgical pillow which has been inflated to a known density is used as the molded cradle. Such a vacuum pillow is seen in U.S. Pat. No. 3,762,404 which is incorporated here by reference. A vacuum pillow is desirable due to its availability and ease of use. It is essential that the leg/hip alignment be capable of being reproduced almost identically at a later point in the surgery. That is, because the present method establishes both pre- and post-replacement reference points, it is imperative that all reference points and measurements be made when the femur is in substantially the same orientation with respect to the hip joint. Otherwise, any measurements and/or reference points established will be less meaningful.

With the patient secured in the lateral decubitus position, the operative leg is laid on the molded cradle. A cradle size of 38 inches by 35.5 inches is preferred. Two folded towels are laid between the leg and the cradle to create additional space in the cradle for the sterile drapes. A standard lateral positioner is attached to each side of the operating table near the foot end while the cradle is still soft. They will stabilize the hardened cradle on the operating table.

The cradle is manually molded to the towels and leg with the hip in full extension. A protective drape is laid over the cradle prior to "prepping" the leg. The cradle must not surround, and thereby capture, the leg, and its proximo-anterior edge must be flattened so as not to interfere with hip flexion during the range of motion trials. The cradle is then hardened by applying suction, and the two folded towels are removed. A protective U-Drape, is laid over the cradle prior to prepping the leg. A stable, rigid cradle is thus formed which will snugly accommodate the leg and several layers of sterile drapes.

After surgically exposing the greater trochanter, a specially notched pin 10, is inserted in the pelvic bone preferably about ½ inch superior to the upper edge of the acetabulum 20.

The specially designed pin 10 is inserted directly into the pelvis 18. (See FIG. 3). The pin 10 is inserted directly into the chuck of the orthopedic drill and driven into the pelvis 18.

The pin 10, according to the present invention, and as shown generally in FIG. 1 includes an axial shaft 22 which is provided with a plurality of weakened areas 24, preferably of reduced cross-section and/or diameter, formed therein such that the shaft 22 may be bent at desired angles, which in the preferred embodiment are approximately 90° angle at a pair of weakened areas 24. This arrangement permits the notched pin 10 to assume plural angular orientations. The length of notched pin 10 preferably ranges from 16 inches to 22 inches with 18 inches being the most preferred length. It should be noted that the 18 inch preferred length is substantially longer than most other known surgical pins due to its contemplated use. The pin 10 is preferably about 5/32 inch in diameter at a plurality of nonweakened areas 26 and about 1/10 inch at the weakened areas 24 of reduced cross-section or diameter. However, these dimensions are merely preferred and could be either larger or smaller according to the circumstances as long as the weakened areas 24 are still capable of being bent to establish the desired reference points. The weakened areas 24 of the pin 10 are preferably equidistantly spaced with respect to each other. In a preferred embodiment, the weakened areas 24 are each about 0.25 inch in length, and are separated by about 0.3125 inch. The shaft will include a blunt end 28 and a sharpened or trochar tipped end 30, the blunt end 28 being capable of being inserted into a conventional orthopedic drill chuck. In a preferred embodiment, an initial portion 25 at the sharpened end of the pin is rigid and free from weakened areas. This initial portion 25 which is free from weakened areas facilitates insertion and maintenance of the pin within a patient's pelvis. A plurality of threads 32 are provided adjacent the sharpened end of the shaft. The threads 32 will ensure stable fixation of the pin 10 in position within the pelvis 18 and prevent migration medially into the pelvis. The pin, at the initial portion 25, is preferably smooth and rigid from the threads 32 to the first weakened area, a distance preferably of about five inches, but could be another appropriate length.

After insertion of the pin 10 within the pelvis 18 at the desired location, the pin 10 is then bent, preferably by hand, at two of the weakened areas 24 in a direction toward the joint 14. The bends are typically made at about 90° angles. However, depending on the geometry of the hip or the size of particular patient, the bends may be either greater or less than 90°. The pin 10 should be bent so that the blunt end 28 is just touching a greater trochanter 34 of the patient. (See FIG. 3). This point of intersection 36 with the greater trochanter 34 is than marked directly on the patient using any convenient means, including but not limited to a dye such as methylene blue, a suture, a staple, tape, or any other suitable marking device which will provide visual indication of the reference point.

As stated above, other configurations of the bent pin may be possible, e.g. an inverted "V" or multiple bends, so that the pin extends from the pelvis to the greater trochanter. Also, the pin may be constructed in multiple pieces wherein the portion normally swung out of the way during operation can actually be removed from and replace on the shaft projecting from the pelvic bone as appropriate.

The angular position of the pin 10 is then locked by means of a locking member 38. The locking member is preferably separate, but could be attached directly to the notched pin 10 if desired. The locking member 38 is semi-rigid and includes a plurality of recesses 40 formed therein. The overall shape of the locking member 38 is immaterial so long as the plurality of recesses 40 are included. However, a flat member, as illustrated, is preferred. The pin 10 is maintained in its bent configuration by attaching the locking member 38 to the notched pin 10 so that the recesses 40 of the locking member 38 encompass the shaft 22 of the pin 10 in two different places seen at 42,44. For instance, if the pin 10 forms a U-shape in its bent configuration (as is preferred), the locking member 38 will engage a pair of "legs" 46,48 of the "U" and maintain the position of the pin 10. (See FIG. 2). It is preferable to use the locking member 38 to ensure that the position of the pin 10 does not change during the surgical hip replacement procedure.

After placement of the locking member 38 onto the pin 10, the bent pin is then rotated away from the vicinity of the hip joint 14 and adjacent femur 12 approximately 180°. (See FIG. 4). This permits the surgeon to carry on with the hip replacement without the pin assembly being in the way. However, it is essential that the pin 10, which is rotated, be maintained in substantially the exact same angular configuration and depth in the pelvic bone 18 as was used to establish the reference point 36 on the greater trochanter 34.

After the femoral head 50 has been removed and fitted with a trial femoral head prosthesis, not shown, and the acetabulum 20 has been reamed, and a trial acetabular component installed, the surgeon conducts what is known as "trial reduction," wherein the optimum size and shape of the prostheses are determined. During the trial reduction, the bent pin 10 is then repositioned by rotating the pin 10 toward the operative site. At this point, the patient's leg is repositioned in the fixed, molded cradle to ensure that the femur 12 is in the same alignment with the hip 14 as when the pre-replacement reference point 36 was established.

The position of the blunt end of the pin 28 with respect to the patient's greater trochanter 34 is then compared with the pre-replacement reference point 36. If the blunt end of the pin 28 is not aligned with the mark on the trochanter, the surgeon knows that the leg length is either too long or too short. To modify leg length, the surgeon removes more bone from the femoral neck, or uses a femoral implant with a longer neck segment.

If, after moving the pin 10 back to its reference point 36, there is a gap between the femur 12 and the pin 28, the surgeon knows that the offset of the joint 14 is not accurate. To correct the offset the surgeon can select a femoral prosthesis with a greater or lesser neck angle or select a socket which can lateralize the joint.

The surgeon may use the pin 10 and the prior reference point 36 at any time during the replacement procedure to ensure that the leg length and/or joint geometry are as desired. Each time a measurement or comparison with the pre-replacement reference point 36 is conducted, the patient's leg must be oriented in substantially the same alignment as when the reference was taken by laying the leg in the molded cradle.

It is further contemplated that a kit for use in aligning the hip of a patient during hip replacement surgery could be packaged. The kit will include the notched surgical pin 10 having a plurality of weakened areas 24, the locking member 38 which is capable of being removably attached to the surgical pin 10 to hold the surgical pin 10 in a fixed angular orientation, and a marking device, not shown, which is capable of placing a visible mark on the patient.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A method for reconfiguring the component parts (i.e., the pelvic bone, femoral head, femur, trochanter and acetabulum) of a hip joint for optimum mechanics of a patient during a hip joint replacement procedure being performed on the patient comprising:

positioning the patient's femur so that the femur is in a specific alignment with respect to the hip joint;

providing a pin having a plurality of weakened areas formed therein along at least a portion of its length, the pin further being capable of being bent at the weakened areas;

inserting the pin into the pelvic bone prior to replacing the hip with a prosthesis;

bending the pin only at least one weakened area;

positioning the end of the pin remote from the pelvic bone so that the remote end is adjacent the leg of the patient;

marking the location of the remote end of the pin with respect to the leg of the patient;

moving the remote end of the pin from the vicinity of the leg without changing the orientation of the pin.

2. A method as claimed in claim 1, including subsequently performing a hip replacement procedure on the patient.

3. A method as claimed in claim 2, including subsequently repositioning the patient's femur into the desired specific configuration with respect to the hip joint.

4. A method as claimed in claim 3, including subsequently repositioning the pin using the marked location as a guide to approximate the optimal configuration of the hip joint.

5. A method as claimed in claim 4, including modifying the alignment of the hip joint after the hip replacement procedure such that the configuration of the hip joint is consistent with the marked location.

6. A method as claimed in claim 1, including marking the location of the pin directly on the trochanter of the patient.

7. A method as claimed in claim 1, including holding the bent pin in a fixed orientation with a locking member.

8. A method as claimed in claim 1, bending the pin to form a substantially U-shape.

9. An instrument for use in reconfiguring the component parts of a hip joint during a hip replacement procedure, comprising:

a surgical pin, the pin formed by a shaft, the shaft having a plurality of weakened areas therein whereby the shaft may be bent at an angle at the weakened areas to permit the pin to be bent to assume a plurality of angular orientations, and a locking member, the locking member being removably attached to the surgical pin to hold the surgical pin in a fixed, bent orientation.

10. The instrument of claim 9, wherein the pin has a sharpened end and a blunt end, and an initial portion at the sharpened end of the pin is rigid and free of weakened areas.

11. The instrument of claim 10 wherein the end adjacent the initial portion is formed with a blunt point.

12. The instrument of claim 10 wherein the sharpened end includes threads thereon.

13. An instrument as claimed in claim 9, wherein said surgical pin is bent at approximately a 90° angle at two of the weakened areas such that the surgical pin is substantially U-shaped.

14. An instrument as claimed in claim 9, wherein the weakened areas are substantially equidistantly spaced with respect to each other.

15. A kit for use in reconfiguring the component geometry of a hip joint during a hip replacement procedure, comprising:

a) a surgical pin, the pin formed by a shaft, the shaft having a plurality of weakened area therein whereby the shaft may be bent at an angle at the weakened area to permit the pin to be bent to assume a plurality of angular orientations, and b) a locking member, the locking member being capable of being removably attached to the pin to hold the pin in a fixed angular orientation.

16. The kit of claim 15 wherein an initial portion at one end of the pin is rigid and free of weakened areas, and the other end is sharpened.

17. The kit of claim 16 wherein the end of the pin adjacent the initial portion is formed with a blunt point, and the sharpened end includes threads thereon.

18. The kit of claim 15 further including a marking device.

* * * * *